United States Patent [19]

Strangio et al.

[11] 4,036,897

[45] July 19, 1977

[54] PRODUCTION OF HEXACHLOROCYCLOPENTADIENE

[75] Inventors: Vincent A. Strangio, Glenridge; Herbert Riegel, Maplewood; Morgan C. Sze, Upper Montclair, all of N.J.

[73] Assignee: The Lummus Company, Bloomfield, N.J.

[21] Appl. No.: 711,632

[22] Filed: Aug. 4, 1976

[51] Int. Cl.$^2$ ............................................. C07C 23/08
[52] U.S. Cl. ................................................ 260/648 C
[58] Field of Search .................................... 260/648 C

[56] References Cited

U.S. PATENT DOCUMENTS 3,649,699  3/1972  Aoki et al. ...................... 260/648 C
3,651,019  3/1972  Asscher et al. .................. 260/648 C
3,748,281  7/1973  Aoki et al. ...................... 260/648 C Primary Examiner—C. Davis
Attorney, Agent, or Firm—Marn & Jangarathis

[57] ABSTRACT

Hexachlorocyclopentadiene is produced by contacting pentane, pentene, cyclopentane or cyclopentene or chlorinated derivatives thereof with a molten salt mixture of cuprous and cupric chloride. Cyclopentadiene can also be employed as an initial feed, in which case the cyclopentadiene is initially chlorinated to effect saturation thereof, followed by contacting of the chloro substituted cyclopentane with a molten salt mixture of cuprous and cupric chloride to produce hexachlorocyclopentadiene.

33 Claims, 3 Drawing Figures

PRODUCTION OF HEXACHLOROCYCLOPENTADIENE

This invention relates to the production of hexachlorocyclopentadiene.

Hexachlorocyclopentadiene is used in the manufacture of pesticides, polymeric resins and plasticizers, and the demand for such a product has been steadily increasing. As a result, there is a need for new and improved processes for producing hexachlorocyclopentadiene.

The principal object of this invention is to provide a new and improved process for producing hexachlorocyclopentadiene.

In accordance with one aspect of the present invention, a $C_5$ hydrocarbon, which is saturated or is mono-olefinically unsaturated, or a chloro substituted derivative thereof, is contacted with a molten salt mixture of cuprous and cupric chloride, with such contacting converting the feed to a reaction effluent containing hexachlorocyclopentadiene.

In accordance with another aspect of the present invention, cyclopentadiene is employed as fresh feed for the ultimate production of hexachlorocyclopentadiene. In accordance with this aspect of the present invention, the cyclopentadiene is initially chlorinated to saturate the double bonds and produce chlorinated cyclopentane, which is then contacted with a molten salt mixture of cuprous and cupric chloride to produce a reaction effluent containing hexachlorocylopentadiene.

The molten salt contains a mixture of cuprous and cupric chloride, and generally also includes a metal chloride melting point depressant which is non-volatile and resistant to the action of oxygen at the process conditions in order to maintain the mixture of copper chloride in molten form. Suitable metal chloride melting point depressants are the alkali metal chlorides, such as potassium and lithium chloride, in particular, but it is to be understood that other metal chlorides and mixtures thereof such as the heavy metal chlorides; i.e., heavier than copper, of Groups I, II, III, and IV of the Periodic Table; e.g., zinc, silver and thallium chloride, may also be employed. The metal chloride melting point depressant is added in an amount sufficient to maintain the salt mixture as a melt at the reaction temperatures, and is generally added in an amount sufficient to adjust the solidification point of the molten salt mixture to a temperature of below about 500° F. In using potassium chloride as a melting point depressant, the composition generally contains from about 20 to about 40%, by weight, of potassium chloride. The molten salt mixture may also contain other reaction promoters, such as, rare earth metal chlorides.

In employing a saturated or mono-olefinically unsaturated $C_5$ hydrocarbon, or chloro substituted derivative thereof, as fresh feed, the $C_5$ hydrocarbon does not have any carbon atoms bonded directly to more than 3 carbon atoms, with the preferred starting materials being either pentene, isopentene, pentane, isopentane, cyclopentane, cyclopentene or the chlorinated derivative thereof, with such chlorinated derivatives generally containing from 1 -5 chlorine atoms.

In effecting the conversion of the starting material to hexachlorocyclopentadiene, the cupric chloride of the molten salt mixture provides chlorine values for the conversion. As should be apparent, the use of cupric chloride for providing chlorine values will result in a continuous depletion of the cupric chloride, and a net production of hydrogen chloride. Therefore, if the process is to be effected on a continuous basis, a provision must be made for regeneration of the cupric chloride and disposal of the hydrogen chloride.

In accordance with one embodiment of the present invention, the molten salt mixture of cupric and cuprous chloride is initially contacted in a separate reaction zone with an oxygen-containing gas and hydrogen chloride to enrich the cupric chloride content of the molten salt. The molten salt, now enriched in cupric chloride, is then employed for converting the hereinabove described feeds to hexachlorocyclopentadiene. The hydrogen chloride present in the reaction effluent may be recovered and recycled to the initial reaction zone to effect recovery thereof by reaction with oxygen and the molten salt to enrich the molten salt in cupric chloride. In this manner, the hydrogen chloride fresh feed provides the chlorine values, with essentially all of the hydrogen chloride being ultimately converted to the reaction product.

In accordance with another embodiment, the molten mixture of cuprous and cupric chloride is contacted in an oxidation reaction zone with molecular oxygen to provide a molten salt enriched in copper oxides; i.e., the molten salt is comprised of cuprous chloride, cupric chloride and copper oxide. The molten salt containing cuprous chloride, cupric chloride and copper oxide is then contacted with the hereinabove described feed and hydrogen chloride and/or chlorine to effect conversion of the feed to hexachlorocyclopentadiene. As a result of the copper oxide being present in the reaction zone for producing hexachlorocyclopentadiene, the liberated hydrogen chloride reacts with the copper oxide to enrich the molten salt in cupric chloride. In this manner, the reaction effluent withdrawn from the reaction zone is essentially free of hydrogen chloride, whereby effectively all of the chlorine values introduced into the reaction zone are utilized for producing chlorinated product.

The production of the hexachlorocyclopentadiene by use of the molten mixture of cuprous and cupric chloride is generally effected at temperatures in the order of from about 750° to about 1000° F, preferably in the order of from about 800° to about 925° F. The reaction pressure may vary from about 1 to about 10 atm.

In accordance with a particularly preferred procedure of the present invention, it has been found that gaseous chlorine should be present during the production of the hexachlorocyclopentadiene in that such presence of chlorine reduces carbon formation. In general, the chlorine/$C_5$ hydrocarbon or chlorohydrocarbon feed ratio should range from 100 to 500% in excess of the stoichiometric ratio required to convert the $C_5$ hydrocarbon or chlorohydrocarbon feed to hexachlorocyclopentadiene product, exclusive of the chlorine required for hydrogen removal. In the case of tetrachlorocyclopentane feed, the chlorine/tetrachlorocyclopentane feed ratio should range from 2 to 6 mole ratio, and preferably from 2 to 3 mole ratio compared to the stoichiometric ratio of 1 required for hexachlorocyclopentadiene production. In such an embodiment, the reaction effluent from the hexachlorocyclopentadiene production zone will contain the excess chlorine in gaseous form, and such gaseous chlorine is recovered from the effluent and recycled to such reaction zone in order to maintain the hereinabove noted excess of gaseous chlorine. The temperature and pressure of the hexachlorocyclopentadiene production reactor, the cupric chloride content of the molten salt can be coordinated to insure that there is a sufficiently high chlorine vapor pressure over the molten salt in order to provide the desired excess of gaseous chlorine in such reactor. Thus, for example, a sufficiently high chlorine vapor ressure to insure such excess can be maintained by controlling the cupric chloride content of the molten salt introduced into the reactor at a molar concentration of from 35 to 50%, preferably 40 to 45% with the cupric chloride to total copper mole ratio correspondingly being from about 0.50 to 0.70, preferably 0.55 to 0.65, and maintaining the reactor at a temperature of from 800° to 925° F at a pressure of from 1 to 5 atm. The maintenance of a high chlorine vapor pressure over the salt is also enhanced by the inclusion of hydrogen chloride in the chlorine recycle stream.

In addition, in accordance with the preferred embodiment, the molten salt introduced into the hexachlorocyclopentadiene production reactor does not contain copper oxide. Thus, the oxidation reactor is operated in a manner such that the molten salt withdrawn therefrom does not contain copper oxide. Such a result is easily accomplished by introducing hydrogen chloride into the oxidation reactor in an amount sufficient to react with the added oxygen values to thereby enrich the salt in cupric chloride, and maintain the salt essentially free of copper oxide. It is to be understood that trace amounts may be present as an impurity.

In general, the oxidation reactor is operated at a temperature from about 800° to about 925° F and at a pressure from about 1 to about 10 atm.

In accordance with the preferred aspect of the present invention, the process is operated in a manner such that the circulating molten salt introduced into the top of the hexachlorocyclopentadiene production reactor has a temperature and a cupric chloride content which is higher than the circulating molten salt introduced into the top of the oxidation reactor, and that the hexachlorocyclopentadiene production reactor is operated at a pressure lower than the pressure of the oxidation reactor. In this manner, a high chlorine vapor pressure can be maintained at the top of the hexachlorocyclopentadiene production reactor to insure the desired excess of chlorine, and a low chlorine vapor pressure, can be maintained at the top of the oxidation reactor to increase the absorption of chlorine by the molten salt and minimize the presence of chlorine values in the gaseous effluent withdrawn from the oxidation reactor. The respective salt concentrations, temperatures and pressure are coordinated to provide for the desired chlorine value recovery in the oxidation reactor and the excess chlorine in the production reactor. In general, the salt introduced into the top of the hexachlorocyclopentadiene production reactor is at a temperature of from 20° to 150° F greater than the temperature of the salt introduced into the oxidation reactor, with the production reactor being operated at a pressure of from 0 to 80 psi less than the oxidation reactor. Similarly, the cupric chloride content of the molten salt introduced into the hexachlorocyclopentadiene production reactor is from 1 to 10 mole % greater than the cupric chloride content of the salt introduced into the oxidation reactor. The above conditions are only illustrative and the proper coordination of conditions is deemed to be within the scope of those skilled in the art from the teachings herein.

The molten salt mixture introduced into the hexachlorocyclopentadiene production reactor generally contains from about 35 to about 50 mol%, and preferably from about 40 to about 45 mol% of cupric chloride. As hereinabove noted, the molten salt can be free of copper oxide; however, if copper oxide is present in the molten salt introduced into the hexachlorocyclopentadiene production reactor, the amount of copper oxide can vary over a wide range and is generally controlled in a manner to provide a quantity thereof sufficient to react with the hydrogen chloride generated in the hexachlorocyclopentadiene production reactor. As representative examples of typical copper oxide contents, there may be mentioned amounts in the order of from 0.1 to 1.5 mole percent. Of course, lower amounts; i.e., only a trace or essentially no copper oxide, or higher amounts could be employed depending upon the amount of conversion of liberated hydrogen chloride desired in the reactor, and the selection of appropriate amounts is deemed to be within the scope of those skilled in the art from the present teachings.

The reaction effluent may also contain chlorinated $C_5$ hydrocarbons which are potentially convertible to hexachlorocyclopentadiene, and such chlorinated $C_5$ hydrocarbons can be recovered and recycled to the hexachlorocyclopentadiene production reactor. In general, such chlorinated $C_5$ hydrocarbons are one or more of the following: $C_5Cl_8$; $C_5HCl_5$; $C_5HCl_7$; and $C_{10}Cl_{10}$. Reaction intermediates such as octachlorocyclopentene are dechlorinated by contact with the molten salt to produce hexachlorocyclopentadiene.

In accordance with another aspect of the present invention, hexachlorocyclopentadiene is produced from cyclopentadiene, as starting material. In accordance with this aspect of the present invention, the cyclopentadiene is initially chlorinated at a relatively low temperature in order to effect saturation thereof. The chlorination of cyclopentadiene in order to effect saturation thereof is a reaction which is generally known in the art, and the particular conditions form no part of the present invention. In general, the chlorination is effected in the liquid phase at a temperature in the order of from about 0° to about 100° C, with the reaction preferably being effected at a temperature below about 60° C. The chlorination is effected in the presence or absence of a suitable diluent which is essentially inert in the reaction, with such diluent generally being a perchlorinated hydrocarbon. The preferred inert diluent is liquid carbon tetrachloride, however, it is to be understood that other inert liquid diluents may also be employed for effecting such chlorination.

The initial chlorination is generally effected with an excess of chlorine in that in accordance with a preferred aspect, the chlorine values required for production of the final product are introduced into the initial chlorination stage. It is to be understood, however, that it is not necessary in all cases to operate with a chlorine excess.

The saturation of the cyclopentadiene with chlorine generally involves the addition of at least two moles of chlorine to saturate the two double bonds, with the chlorinated product containing generally at a minimum 4 chlorine atoms per mole of cyclopentadiene, with the product generally containing, at an average, of about 4 to 4.5 chlorine atoms per mole of cyclopentadiene.

Hydrogen chloride is also formed in the reaction, and a reaction product of chlorinated cyclopentadiene, containing at the minimum four chlorine atoms per mole of cyclopentadiene, and hydrogen chloride and excess chlorine, if any, is then introduced into the hexachlorocyclopentadiene production reactor for contact with the molten salt mixture of cuprous and cupric chloride to effect production of hexachlorocyclopentadiene. As hereinabove noted, in accordance with a preferred aspect, the molten salt is essentially free of copper oxide, and the reaction conditions are controlled to provide an excess of chlorine in the reactor in order to minimize carbon production.

The reaction effluent withdrawn from the hexachlorocyclopentadiene production reactor, includes hexachlorocyclopentadiene reaction product, unreacted starting material, reaction intermediates, hydrogen chloride and chlorine, with such effluent being introduced into a separation and recovery zone. In the separation and recovery zone, hexachlorocyclopentadiene is recovered as product, with unreacted starting material and reaction intermediate being recovered and recycled to the hexachlorocyclopentadiene production reactor.

The chlorine and hydrogen chloride present in the effluent may be recovered in admixture with each other, or as separate streams. The net hydrogen chloride, whether recovered separately or in admixture with chlorine, is introduced into an oxidation reactor along with molecular oxygen and molten salt recovered from the hexachlorocyclopentadiene production reactor wherein the hydrogen chloride and oxygen react with the molten salt to effect production of cupric chloride. The cupric chloride enriched salt is then recycled to the hexachlorocyclopentadiene production reactor.

The chlorine recovered from the reaction effluent is then recycled to the hexachlorocyclopentadiene production reactor in order to insure an excess of chlorine therein.

In the case where hydrogen chloride and chlorine are recovered in admixture with each other, such a mixture is recycled to both the chlorination and the oxidation reactor, wherein the hydrogen chloride reacts with the oxygen and the molten salt, as hereinabove described, and wherein the chlorine reacts with cuprous chloride to also produce cupric chloride. The portion of the mixture of chlorine and hydrogen chloride recycled to the hexachlorocyclopentadiene production reactor insures an excess of chlorine therein to reduce carbon formation.

As should be apparent, the overall process involves reaction of chlorine and cyclopentadiene to produce as reaction product-hexachlorocyclopentadiene. The hydrogen chloride intermediate generated in the initial chlorination step and in the hexachlorocyclopentadiene production reactor is effectively recovered by reaction with the molten salt in the oxidation reactor to enrich the cupric chloride content of the molten salt, with such enriched molten salt then being employed to effect chlorination of the chlorinated cyclopentadiene reaction intermediate for ultimate production of hexachlorocyclopentadiene. Thus, by introducing chlorine and cyclopentadiene as fresh feed, the cyclopentadiene is ultimately converted to hexachlorocyclopentadiene.

In accordance with another aspect of the present invention, instead of using chlorine as fresh feed, the fresh feed is hydrogen chloride. In such an aspect of the present invention, hydrogen chloride, as fresh feed, is introduced into the oxidation reactor along with oxygen, wherein the hydrogen chloride and oxygen react with the molten salt to effect enrichment thereof in cupric chloride. The hydrogen chloride is introduced in an amount to provide the total chlorine values for converting cyclopentadiene to hexachlorocyclopentadiene; i.e., at least 6 atoms of chlorine per mole of cyclopentadiene fresh feed.

The molten salt enriched in cupric chloride is then introduced into the hexachlorocyclopentadiene production reactor along with the effluent from the reactor for chlorinating cyclopentadiene, which includes chlorinated cyclopentadiene and hydrogen chloride. In the reactor, the chlorinated cyclopentadiene intermediate is chlorinated by the cupric chloride of the molten salt to hexachlorocyclopentadiene, and in addition, chlorine values are stripped from the salt to provide net chlorine requirements for the initial chlorination of the cyclopentadiene.

The reaction effluent includes the hexachlorocyclopentadiene reaction product, unreacted starting material, reaction intermediates potentially convertible to the reaction product, hydrogen chloride produced in the initial chlorination reaction and in hexachlorocyclopentadiene production and chlorine, with such chlorine being present in an amount at least sufficient to provide the chlorine requirements for the initial chlorination of cyclopentadiene; i.e., at least 4 chlorine atoms per mole of cyclopentadiene.

The net hydrogen chloride produced in the initial chlorination of cyclopentadiene and hexachlorocyclopentadiene production is recovered from the effluent and introduced into the oxidation reactor along with fresh feed hydrogen chloride wherein such chlorine values are recovered by enriching the cupric chloride content of the molten salt. The net chlorine present in the effluent is recovered and inroduced into the initial chlorination reactor to effect chlorination of cyclopentadiene to the chlorinated cyclopentadiene reaction intermediate which is subsequently introduced into the hexachlorocyclopentadiene production reactor.

Thus, in accordance with this aspect of the present invention, hydrogen chloride provides the chlorine values for converting cyclopentadiene to hexachlorocyclopentadiene, with the hydrogen chloride fresh feed being introduced into the oxidation reactor and the cyclopentadiene fresh feed being introduced into the initial chlorination reactor.

In accordance with the various embodiments of the present invention, the reaction effluent withdrawn from the hexachlorocyclopentadiene production zone may also contain chlorinated products which are not potentially and/or economically convertible to the desired product. Such reaction products may be burned in order to recover the chlorine values thereof as chlorine and/or hydrogen chloride, generally a mixture of chlorine and hydrogen chloride, and the combustion effluent can be introduced into the oxidation zone to recover such chlorine values by enriching the cupric chloride content of the molten salt.

The present invention will be further described with respect to embodiments thereof illustrated in the accompanying drawings, wherein.

Figure 1:
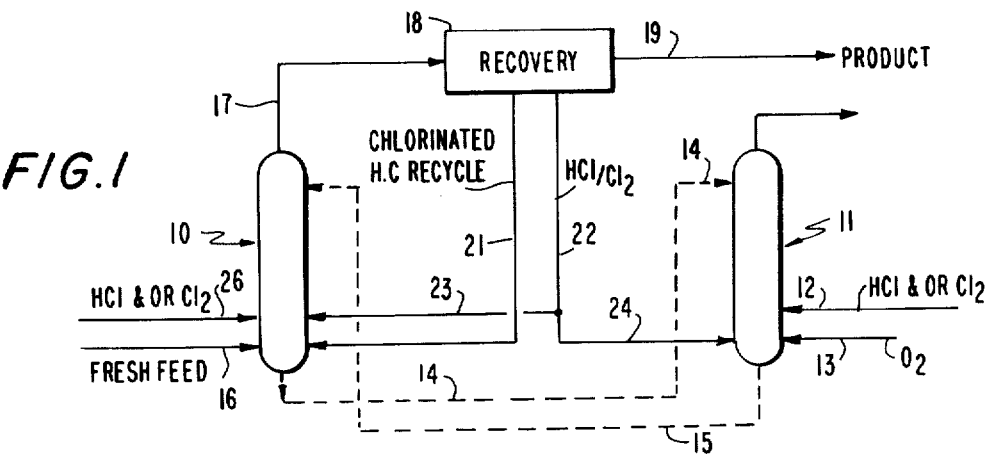
FIG. 1 is a simplified schematic flow diagram of an embodiment of the present invention.

Referring now to FIG. 1, there is illustrated a simplified schematic flow diagram for illustrating the present invention wherein hexachlorocyclopentadiene is produced by the use of molten copper chlorides. The reaction system includes a hexachlorocyclopentadiene production reactor schematically indicated as 10 and an oxidation reactor, schematically indicated as 11.

As hereinabove described, the chlorine values for producing hexachlorocyclopentadiene may be provided by the use of either hydrogen chloride and/or chlorine, with such hydrogen chloride and/or chlorine being introduced into either the hexachlorocyclopentadiene production reactor or the oxidation reactor. In addition, as hereinabove described, the overall invention can be practiced with either copper oxide being present in the molten salt introduced into the hexachlorocyclopentadiene production reactor or in accordance with the preferred procedure wherein the molten salt introduced into the hexachlorocyclopentadiene production reactor does not include copper oxide.

In accordance with the preferred procedure, hydrogen chloride in line 12 and a molecular oxygen-containing gas, such as air, in line 13 are introduced into the oxidation reactor 11 wherein the hydrogen chloride and oxygen are countercurrently contacted with a molten mixture of cuprous and cupric chloride, which further contains a melting point depressant, such as potassium chloride, introduced through line 14. The hydrogen chloride is introduced in an amount sufficient to provide the chlorine values for converting the fresh feed to hexachlorocyclopentadiene, and the oxygen values are introduced in an amount sufficient to effect conversion of the hydrogen chloride, by reaction with the cuprous chloride present in the molten salt, into cupric chloride, without production of a molten salt which includes copper oxide. As a result of the countercurrent contact in the oxidation reactor 11, the molten salt is enriched in cupric chloride, with such molten salt being withdrawn from oxidation reactor 11 through line 15 and introduced into the hexachlorocyclopentadiene production reactor 10. The molten salt, as hereinabove described, is essentially free of copper oxide.

A gaseous effluent, containing water vapor, nitrogen, any unrecovered products, such as carbon oxide(s), introduced with a combustion effluent from the burning of chlorinated by-products, if introduced, equilibrium amounts of hydrogen chloride and some minor amounts of chlorine, is withdrawn from oxidation reactor 11 and may be further treated to recover hydrogen chloride and/or chlorine, or vented to the atmosphere after appropriate treatment; e.g., neutralization.

A fresh feed, which is saturated or mono-olefinically unsaturated $C_5$ hydrocarbon, or chloro substituted derivative thereof is introduced into the hexachlorocyclopentadiene production reactor 10 through line 16. As a result of the countercurrent contact between the molten salt introduced through line 15, and the fresh feed introduced through line 16, such fresh feed is converted to hexachlorocyclopentadiene. The temperatures and pressures employed in the hexachlorocyclopentadiene production reactor 10 are as hereinabove described. In addition, in accordance with the preferred embodiment, the conditions are maintained such that there is a high chlorine vapor pressure over the molten salt whereby the conversion is effected in an atmosphere of excess chlorine.

A reaction effluent is withdrawn from reactor 10 through line 17, and such reaction effluent includes hexachlorocyclopentadiene reaction product, unreacted fresh feed, and reaction intermediates which are potentially convertible to hexachlorocylopentadiene. In addition, such reaction effluent includes chlorine as a result of maintaining an excess of chlorine in the reactor 10, as well as hydrogen chloride, that formed as a reactor intermediate and that recycled to reactor 10 for the primary purpose of contributing to the maintenance of excess chlorine in reactor 10.

The reaction effluent in line 17 is introduced into a separation and recovery zone, schematically indicated as 18. In separation and recovery zone 18, hexachlorocyclopentadiene is recovered as a reaction product through line 19. In addition, reaction intermediate potentially convertible to hexachlorocyclopentadiene, as well as unreacted starting material, are recovered in separation and recovery zone 18 through line 21 and recycled to the reactor 10.

The hydrogen chloride and chlorine present in the reaction effluent are recovered in the separation and recovery zone 18 through line 22, with a portion thereof being introduced into the reactor 10 through line 23 to maintain excess chlorine therein. In addition, a portion of the hydrogen chloride and chlorine recovered from the reaction effluent are introduced into the oxidation reactor 11 through line 24 wherein the hydrogen chloride is recovered by reaction with the oxygen and the molten salt to produce cupric chloride, and wherein the chlorine is recovered by reaction with the molten salt to also produce cupric chloride. In this manner, the hydrogen chloride generated in reactor 10 is recovered in reactor 11 for ultimate use of the chlorine values thereof for production of hexachlorocyclopentadiene. The net hydrogen chloride production in reactor 10 is introduced into reactor 11 through line 24. As an alternative, the hydrogen chloride and chlorine can be recovered as separate streams, with the net hydrogen chloride being introduced into reactor 11 to recover the chlorine values therefrom, and the chlorine being introduced into reactor 10 in order to maintain an excess of chlorine. As a further alternative, and a less preferred embodiment, the reactor 10 may be operated without an excess of chlorine, in which case the reaction effluent withdrawn from reactor 10 would be essentially free of chlorine, and the chlorine recycle to reactor 10 would be eliminated.

As an alternative embodiment, chlorine can be used as fresh feed, and such chlorine could be introduced into reactor 11 through line 12 whereby the chlorine would react with the molten salt to enrich the molten salt in cupric chloride. The enriched molten salt would then flow to reactor 10 wherein the fresh feed would be chlorinated, as hereinabove described. The hydrogen chloride reaction intermediate present in the effluent withdrawn from reactor 10 would be ultimately recovered and recycled to reactor 11 to recover the chlorine values therefrom by reaction between the hydrogen chloride, molecular oxygen introduced through line 13, and the cuprous chloride of the molten salt introduced through line 14. In this embodiment, the reactor 10 may be operated with and/or without an excess of chlorine. Thus, in this alternative embodiment, chlorine is employed as net feed for providing chlorine values, with chlorine values being ultimately recovered for production of hexachlorocyclopentadiene.

As still another alternative embodiment, as hereinabove described, hydrogen chloride or chlorine could be introduced through line 26 into the hexachlorocyclopentadiene production reactor 10. In the case where chlorine is introduced as fresh feed, the reactor 10 may be operated with or without an excess of chlorine, as hereinabove described. The reaction effluent withdrawn from reactor 10 would contain hydrogen chloride reaction intermediate, with such hydrogen chloride being recycled to the oxidation reactor 11 to recover the chlorine values thereof by reaction between oxygen and the cuprous chloride of the molten salt introduced through line 14. In this embodiment, chlorine values are directly added to the hexachlorocyclopentadiene production reactor 10, with chlorine values present in the reaction effluent being ultimately recovered and utilized for production of the final product.

In the case where hydrogen chloride is introduced into reactor 10 through line 26 as fresh feed, the molten salt introduced into reactor 10 through line 15 would contain copper oxide in order to effectively convert the hydrogen chloride to chlorine for effecting chlorination of the fresh feed. In such an embodiment, the reaction effluent withdrawn from reactor 10 would contain only equilibrium amounts of hydrogen chloride which could be recovered, as hereinabove described for recycle to the oxidation reactor 11. In this embodiment, oxygen is introduced into the oxidation reactor 11 primarily for the purpose of generation a molten salt which contains copper oxide for ultimate introduction into the hexachlorocyclopentadiene production reactor 10.

As still another alternative embodiment, hydrogen chloride and/or chlorine could be introduced directly into the hexachlorocyclopentadiene production reactor 10 and/or the oxidation reactor 11, with the oxidation reactor 11 being operated in a manner such that the molten salt withdrawn therefrom includes copper oxide. Thus, the molten salt introduced into the hexachlorocyclopentadiene production reactor 10 would include copper oxide, which would react with the hydrogen chloride introduced as fresh feed, or generated therein as reaction intermediate, whereby the reaction effluent withdrawn from the hexachlorocyclopentadiene production reactor 10 would contain only equilibrium amounts of hydrogen chloride, thereby eliminating the necessity for recovering and recycling to the oxidation reactor 11 large amounts of hydrogen chloride generated as reaction intermediate in reactor 10.

The embodiments in which copper oxide is present in the molten salt introduced into the hexachlorocyclopentadiene production reactor 10 are less preferred in that such presence of copper oxide may generate oxygenated reaction intermediate which are not potentially convertible to the hexachlorocyclopentadiene reaction product thereby lowering overall yields.

As should be apparent, from the hereinabove description of alternative embodiments for producing hexachlorocyclopentadiene by the use of molten salts, essentially all of the chlorine values introduced into the system are eventually utilized for production of the hexachlorocyclopentadiene final product.

Figure 2:
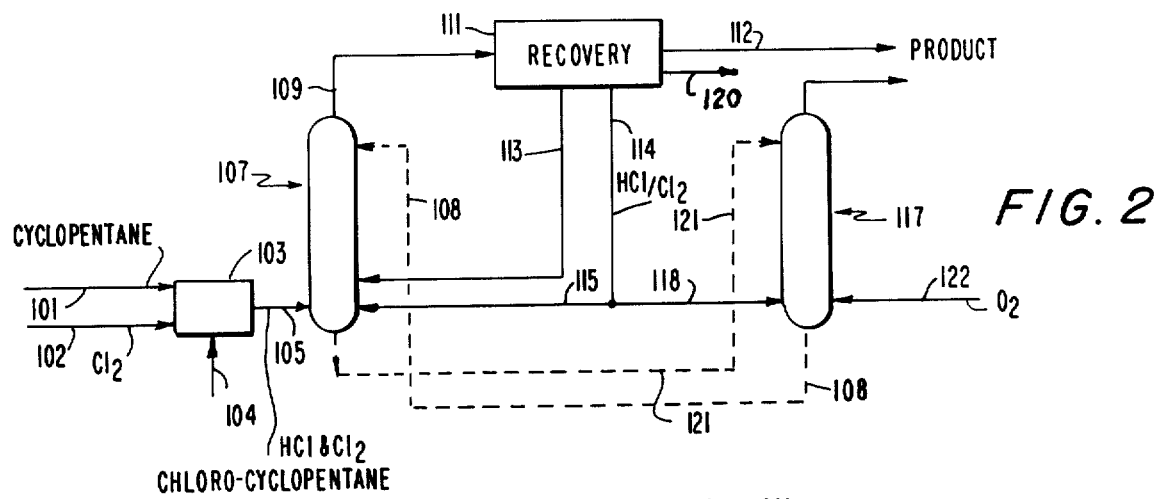
FIG. 2 is a simplified schematic flow diagram of another embodiment of the present invention.

Another embodiment of the present invention is illustrated in FIG. 2, with such embodiment being particularly directed to the production of hexachlorocyclopentadiene from cyclopentadiene as fresh feed, utilizing chlorine to provide the chlorine values for the chlorination.

Referring now to FIG. 2, cyclopentadiene fresh feed in line 101 and chlorine fresh feed in line 102 are introduced into an initial chlorination reactor, schematically indicated as 103. The chlorine is introduced in an amount sufficient to provide chlorine values for saturating the cyclopentadiene; i.e., at least 2 moles of chlorine per mole of cyclopentadiene in that the use of at least 2 moles of chlorine provides at least 4 atoms of chlorine substituted on the cyclopentadiene. The chlorine is preferably introduced in an amount of at least 3 moles to provide sufficient chlorine fresh feed for producing the hexachlorocyclopentadiene final product. The initial chlorination reactor 103 is operated as hereinabove described; i.e., at a low temperature and in the presence of a suitable diluent, such as carbon tetrachloride, introduced through line 104.

A reaction effluent is withdrawn from reactor 103 through line 105, and such reaction effluent includes chloro substituted cyclopentadiene with such chloro substituted cyclopentadiene containing at least 4 atoms of chlorine, and generally an average of 4 to 4.5 atoms of chlorine, as well as hydrogen chloride and the excess chlorine introduced into the initial chlorination reactor, which is required for the production of the final product. Carbon tetrachloride diluent is preferably separated (not shown) from the effluent from reactor 103 prior to introduction thereof into reactor 107.

The effluent present in line 105 is introduced into a hexachlorocyclopentadiene production reactor, schematically indicated as 107, wherein the effluent is contacted with a molten salt mixture, including cuprous chloride, cupric chloride, and a melting point depressant, such as potassium chloride, introduced through line 108. As hereinabove described, in accordance with the preferred embodiment, the molten salt introduced through line 108 is essentially free of copper oxide. The reactor 107 is operated at temperatures and pressures, as hereinabove described, with the reactor 107 preferably being operated with an excess of chlorine in order to reduce the formation of carbon.

A reaction effluent is withdrawn from reactor 107 through line 109, and the reaction effluent includes hexachlorocyclopentadiene reaction product, unreacted chloro substituted cyclopentadiene, reaction intermediates potentially convertible to hexachlorocyclopentadiene, chlorine, as a result of maintaining an excess of chlorine in reactor 107, and hydrogen chloride present in the effluent introduced into reactor 107 through line 105 and generated in reactor 107, and that recycled via line 115. The effluent in line 109 is introduced into a separation and recovery zone, schematically indicated as 111, in order to recover various components thereof.

Hexachlorocyclopentadiene reaction product is separated in zone 111 and recovered as product through line 112. Unreacted chlorinated cyclopentadiene, as well as reaction intermediates, are recovered in zone 111 through line 113 and are recycled to the reactor 107. Heavier chlorinated hydrocarbons are recovered through line 120 and such heavies can be burned to recover chlorine values, as hereinabove described.

Hydrogen chloride and chlorine present in the effluent in line 109 are recovered in zone 111 through line 114, and a portion thereof introduced through line 115 into the reactor 107 in order to maintain an excess of chlorine in reactor 107.

A further portion of the hydrogen chloride and chlorine in line 114 is introduced into an oxidation reactor, schematically indicated as 117 in order to recover the chlorine values thereof. The amount of hydrogen chloride introduced into reactor 117 through line 118 represents the net hydrogen chloride produced in reactors 103 and 107.

A molten salt mixture of cuprous chloride and cupric chloride is withdrawn from reactor 107 through line 121 and introduced into the oxidation reactor 117. In addition, an oxygen-containing gas, such as air, is introduced into reactor 117 through line 122. In oxidation reactor 117, net hydrogen chloride generated in reactors 103 and 107 and introduced into oxidation reactor 117 through line 118, is recovered by reaction with molecular oxygen and the cuprous chloride of the molten salt to effect enrichment of the molten salt in cupric chloride. In addition, any chlorine present in line 118 is converted to cupric chloride. A molten salt, enriched in cupric chloride is withdrawn from oxidation reactor 117 for introduction into reactor 107 through line 108.

As should be apparent, in accordance with this embodiment, the total chlorine required for producing hexachlorocyclopentadiene from cyclopentadiene can be introduced into the initial chlorination reactor 103, with a portion of such total chlorine values being converted in reactors 103 and 107 to hydrogen chloride, with such hydrogen chloride ultimately being recovered and employed for producing hexachlorocyclopentadiene. In this manner, essentially all of the chlorine values introduced into the system are ultimately converted to usable product.

Figure 3:
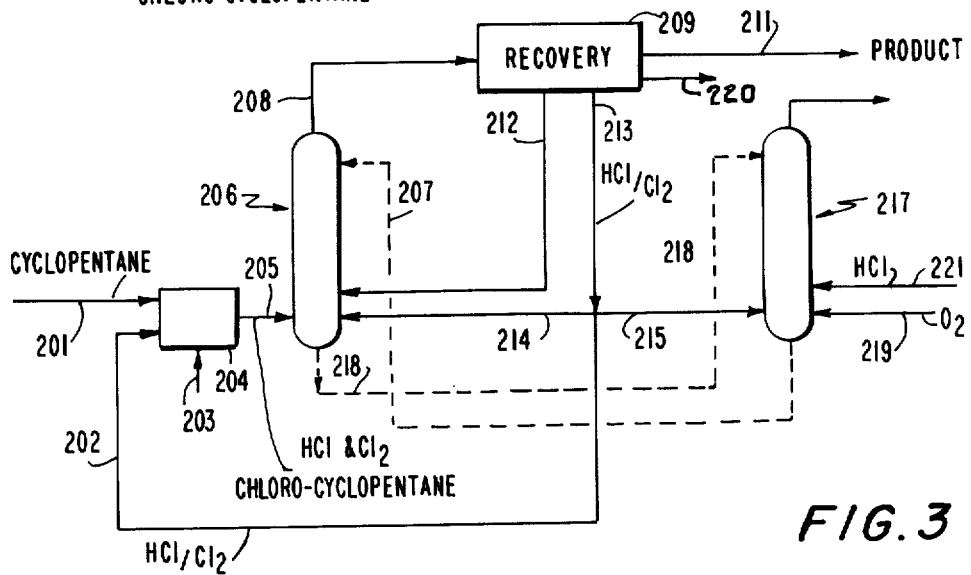
FIG. 3 is a simplified schematic flow diagram of a further embodiment of the present invention.

Another embodiment of the present invention is illustrated in FIG. 3, in which embodiment hydrogen chloride is employed as net feed for providing chlorine values to the process.

Referring to FIG. 3, cyclopentadiene fresh feed in line 201, chlorine, obtained as hereinafter described, in line 202, and a suitable diluent, such as carbon tetrachloride in line 203 are introduced into an initial chlorination reactor, schematically indicated as 204, wherein, as hereinabove described, the cyclopentadiene is chlorinated to produce a saturated chloro substituted cyclopentadiene. The chlorination in reactor 204 is effected as hereinabove described, and the reaction effluent is withdrawn through line 205, with such effluent including chloro substituted cyclopentadiene, having at least 4 atoms of chlorine per mole, chlorine and hydrogen chloride reaction intermediate.

The effluent in line 205 is introduced into a hexachlorocyclopentadiene production reactor, schematically indicated as 206, wherein the effluent is contacted with a molten salt mixture of cuprous chloride and cupric chloride, which further contains a melting point depressant, such as potassium chloride, and which is essentially free of copper oxide, introduced through line 207. The hexachlorocyclopentadiene production reactor is operated as hereinabove described to effect production of hexachlorocyclopentadiene, with such reactor preferably being operated with an excess of chlorine in order to reduce production of carbon.

An effluent, containing hexachlorocyclopentadiene reaction product, unreacted starting material, reaction intermediates potentially convertible to hexachlorocyclopentadiene, hydrogen chloride introduced with the effluent through line 205 and generated in reactor 206, and introduced via line 214, and chlorine, present as excess in reactor 206, is withdrawn through line 208 and introduced into a separation and recovery zone, schematically indicated as 209. Hexachlorocyclopentadiene reaction product is recovered in zone 209 through line 211. Heavier chlorinated hydrocarbons are recovered through line 220. Reaction intermediates potentially convertible to hexachlorocyclopentadiene, as well as unreacted starting material, is recovered in zone 209 and recycled to hexachlorocyclopentadiene production reactor 206 through line 212.

Hydrogen chloride and chlorine present in the reaction effluent in line 208 is recovered from separation and recovery zone 209 through line 213. The hydrogen chloride present in line 213 is the hydrogen chloride reaction intermediate generated in reactors 204 and 206 and that hydrogen chloride recycled to reactor 206 via line 214, and the chlorine present in line 213 includes net chlorine produced from hydrogen chloride starting material, as hereinafter described, and which is employed for effecting the initial chlorination of the cyclopentadiene feed. A portion of the hydrogen chloride and chlorine present in line 213 is introduced into the initial chlorination reactor 204 through line 202, with such portion being sufficient to meet the chlorine requirements for reactor 204. A further portion of the hydrogen chloride and chlorine present in line 213 is introduced into reactor 206 through line 214 in order to maintain an excess of chlorine in reactor 206. A further portion of the hydrogen chloride and chlorine present in line 213 is introduced through line 215 into an oxidation reactor, schematically indicated as 217. The hydrogen chloride present in line 215, which is introduced into oxidation reactor 217, is the net hydrogen chloride produced in reactors 204 and 206 from the chlorination of the cyclopentadiene starting material.

Molten salt, containing cuprous chloride and cupric chloride, as well as the melting point depressant, withdrawn from reactor 206 through line 218 is introduced into the oxidation reactor 217. In addition, oxygen in line 219 and hydrogen chloride, as fresh feed, in line 221, is introduced into the oxidation reactor 217.

The hydrogen chloride introduced into reactor 217 through line 221 is provided in an amount sufficient to meet the chlorine requirements for converting the cyclopentadiene to hexachlorocyclopentadiene. The oxygen introduced through line 219 is provided in an amount sufficient to convert the hydrogen chloride introduced into reactor 217 into cupric chloride without producing net copper oxide.

In reactor 217, the molten salt introduced through line 218 countercurrently contacts the hydrogen chloride introduced through lines 215 and 221, the oxygen introduced through line 219, and any chlorine present in line 215, and as a result of such contact, the chlorine values are recovered by enriching the molten salt in cupric chloride.

A molten salt enriched in cupric chloride is withdrawn from reactor 217 through line 207 and introduced into reactor 206. The cupric chloride content of the molten salt in reactor 207 is sufficient to provide the chlorine values for effecting conversion of the chloro substituted cyclopentadiene reaction intermediate introduced through line 205 into hexachlorocyclopentadiene, and also produce net chlorine for ultimate introduction into reactor 204 for effecting the initial chlorination of the cyclopentadiene fresh feed. Thus, in reactor 206, the cupric chloride is utilized for effecting chlorination of the chloro substituted cyclopentadiene introduced through line 205 and to also produce net chlorine in the effluent in line 208 for ultimate recovery and introduction into the chlorination reactor 204 to effect chlorination of cyclopentadiene to saturated chlorinated intermediate.

As should be apparent, from the hereinabove description of the embodiment illustrated in FIG. 3, hydrogen chloride is introduced as net feed into the oxidation reactor 217, with such hydrogen chloride providing the chlorine values for effecting the initial chlorination of the cyclopentadiene, and the subsequent chlorination of the reaction intermediate produced in the initial chlorination reactor 204 for ultimate production of hexachlorocyclopentadiene from cyclopentadiene. In addition, all the chlorine values are effectively recovered and utilized for the production of hexachlorocyclopentadiene.

The above embodiment may also be modified within the spirit and scope of the present invention. Thus, for example, hydrogen chloride and chlorine can be separately recovered in separation zone 209 for introduction into the appropriate reactors.

The invention will be further described with respect to the following examples; however, the scope of the invention is not to be limited thereby.

EXAMPLE I

The following is illustrative of the embodiment of the present invention described with reference to FIG. 2.

Reactor 107 is operated at pressure of 28 psia and reactor 117 at a pressure of 80 psia.

Molten salt is introduced into reactor 107 at a temperature of 900° F and into reactor 117 at a temperature of 839° F.

The embodiment is described only with reference to the effluent from the initial chlorination reactor as net feed to the process. In addition, heavies are recovered as net product, rather than being burned to recover chlorine values which can be recovered in the oxidation reactor.

Molten salt is introduced into reactor 206 at a temperature of 900° F and into reactor 217 at a temperature of 814° F.

The embodiment is described only with reference to the effluent from the initial chlorination reactor as net feed to the process. In addition, heavies are recovered as net product.

| Stream Component | 221 MPH | 219 MPH | 215 MPH | 218 MPH | 207 MPH | 201 MPH | 202 MPH | 205 MPH | 212 MPH | 214 MPH | 208 MPH | Product MPH |
|---|---|---|---|---|---|---|---|---|---|---|---|---|
| $C_5H_{5.5}Cl4.5$ | | | | | | | | 11.9 | | | | |
| $C_5Cl_6$ | | | | | | | | | | | 11.45 | 11.45 |
| $C_5Cl_8$ | | | | | | | | | | 0.22 | 0.22 | |
| $C_5H_6$ | | | | | | 11.9 | | | | | | |
| Heavies | | | | | | | | | | | 0.38 | |
| H Cl | 82.3 | 71.5 | | | | 144.4 | 150.4 | | 58.6 | 274.5 | | |
| Cl2 | | | 19.1 | | | | 38.7 | 9.0 | | 15.7 | 73.5 | |
| H2O | | 9.1 | | | | | | | | | | |
| O2 | | 64.4 | | | | | | | | | | |
| N2 | | 243.6 | | | | | | | | | | |
| K Cl | | | | 1215 | 1215 | | | | | | | |
| Cu Cl | | | | 926 | 745 | | | | | | | |
| Cu Cl2 | | | | 1619 | 1800 | | | | | | | |
| TOTAL | 82.3 | 317.1 | 90.6 | 3760 | 3760 | 11.9 | 183.1 | 171.3 | 0.22 | 74.3 | 360.1 | 11.45 |
| Temp °F | 100 | 325 | 100 | 814 | 900 | 70 | 100 | 100 | 250 | 100 | 500 | 150 |
| Pressure psia | 80 | 80 | 80 | 76 | 25 | 15 | 15 | 28 | 28 | 28 | 25 | 15 |

The present invention is particularly advantageous in that hexachlorocyclopentadiene is effectively produced without production of unwanted hydrogen chloride by-product. In addition, either chlorine or hydrogen chloride can be employed to provide the chlorine requirements for the process.

Numerous modifications and variations of the present invention are possible in light of the above teachings and, therefore, within the scope of the appended claims, the invention may be practiced otherwise than as particularly described.

What is claimed is:

1. A process for producing hexachlorocyclopentadiene, comprising:
    contacting in a hexachlorocyclopentadiene production zone a feed selected from the group consisting of saturated $C_5$ hydrocarbons, mono-olefinically unsaturated $C_5$ hydrocarbons and chloro substituted derivatives of such saturated and mono-olefinically unsaturated $C_5$ hydrocarbons, with a molten salt mixture of cuprous and cupric chloride to produce an effluent containing hexachlorocyclopentadiene.

2. The process of claim 1 wherein the molten mixture further contains copper oxide.

3. The process of claim 2 wherein a member selected from the group consisting of chlorine, hydrogen chloride and mixtures thereof is introduced into the hexachlorocyclopentadiene production zone, molten salt

| Stream Component | 122 MPH | 118 MPH | 121 MPH | 108 MPH | 101 MPH | 102 MPH | 105 MPH | 113 MPH | 115 MPH | 109 MPH | 112 MPH |
|---|---|---|---|---|---|---|---|---|---|---|---|
| $C_5H_{5.5}Cl4.5$ | | | | | | | 11.9 | | | | |
| $C_5Cl_6$ | | | | | | | | | | 11.45 | 11.45 |
| $C_5Cl_8$ | | | | | | | | | 0.22 | 0.22 | |
| Heavies | | | | | | | | | | 0.38 | |
| $C_5H_6$ | | | | | 11.9 | | | | | | |
| H Cl | | 72.3 | | | | | 6.0 | | 180.2 | 251.7 | |
| Cl2 | | 6.7 | | | | 38.8 | 9.0 | | 16.7 | 23.4 | |
| H2O | 5.5 | | | | | | | | | | |
| O2 | 30.7 | | | | | | | | | | |
| N2 | 116.3 | | | | | | | | | | |
| K Cl | | | 987 | 987 | | | | | | | |
| Cu Cl | | | 987 | 909 | | | | | | | |
| Cu Cl2 | | | 1309 | 1387 | | | | | | | |
| TOTAL | 152.5 | 79.0 | 3283 | 3283 | 11.9 | 38.8 | 26.9 | 0.22 | 196.9 | 287.2 | 11.45 |
| Temp °F | 325 | 100 | 339 | 900 | 70 | 70 | 100 | 250 | 100 | 500 | 150 |
| Pressure psia | 80 | 80 | 76 | 25 | 15 | 15 | 28 | 28 | 28 | 25 | 15 |

EXAMPLE II

The following is illustrative of the embodiment of the present invention described with reference to FIG. 3.

Reactor 206 is operated at pressure of 25 psia and reactor 217 at a pressure of 80 psia.

being withdrawn from the hexachlorocyclopentadiene production zone and being introduced into an oxidation zone wherein the molten salt is contacted with molecular oxygen to enrich the salt in copper oxide, molten salt enriched in copper oxide being passed from the oxidation zone to the hexachlorocyclopentadiene production zone.

4. The process of claim 1 wherein the hexachlorocyclopentadiene production zone is operated at a temperature of from about 750° to about 1000° F.

5. The process of claim 4 wherein gaseous chlorine is introduced into the hexachlorocyclopentadiene production zone.

6. The process of claim 5 wherein molten salt is withdrawm from the hexachlorocyclopentadiene production zone and introduced into an oxidation zone wherein the salt is contacted with hydrogen chloride and oxygen to enrich the molten salt in cupric chloride, and recycling enriched molten salt to the hexachlorocyclopentadiene production zone.

7. The process of claim 6 wherein gaseous chlorine is maintained in the hexachlorocyclopentadiene production zone in an amount of from 100 to 500% in excess of stoichiometric requirements for producing hexachlorocyclopentadiene from the feed exclusive of the chlorine required for hydrogen removal from the feed molecule.

8. The process of claim 7 wherein the feed is a chloro substituted cyclopentane containing at least 4 atoms of chlorine.

9. The process of claim 8 wherein the effluent withdrawn from the hexachlorocyclopentadiene production zone contains chlorine and hydrogen chloride, at least a portion of the chlorine present in the effluent being recovered and recycled to the hexachlorocyclopentadiene production zone to maintain the excess of chlorine and at least a portion of the hydrogen chloride present in the effluent being recovered and recycled to the oxidation zone for recovery therein by reaction with oxygen to enrich the cupric chloride content of the molten salt.

10. The process of claim 9 wherein the hexachlorocyclopentadiene production zone is operated at a temperature of from 800° to 925° F and a pressure of from 1 to 10 atm. and the oxidation zone is operated at a temperature of from 800° to 925° F and a pressure of from 1 to 10 atm.

11. The process of claim 10 wherein molten salt introduced into the hexachlorocyclopentadiene production zone has a cupric chloride content and is at a temperature which are higher than the cupric chloride content and the temperature of the salt introduced into the oxidation zone and the hexachlorocyclopentadiene production zone is operated at a pressure lower than the pressure of the oxidation zone.

12. The process of claim 11 wherein the molten salt introduced into the hexachlorocyclopentadiene production zone has a cupric chloride content of from about 35 to 50 mol percent.

13. The process of claim 12 wherein a mixed stream of chlorine and hydrogen chloride is recovered from the effluent, a first portion of the mixed stream being introduced into the hexachlorocyclopentadiene production zone to maintain the excess of chlorine and a second portion being introduced into the oxidation zone to recover net hydrogen chloride generated in the production of hexachlorocyclopentadiene.

14. The process of claim 12 wherein the effluent includes unreacted feed and reaction intermediates convertible to hexachlorocyclopentadiene which are recovered and recycled to the hexachlorocyclopentadiene production reactor.

15. A process for producing hexachlorocyclopentadiene, comprising:
contacting in an initial chlorination zone, cyclopentadiene and chlorine fresh feed to saturate the double bonds and produce a first effluent containing chloro substituted cyclopentane containing at least 4 atoms of chlorine and hydrogen chloride;
introducing the first effluent into a hexachlorocyclopentadiene production zone wherein the first effluent is contacted with a molten salt mixture of cuprous chloride and cupric chloride, to produce a second effluent containing hexachlorocyclopentadiene and hydrogen chloride;
recovering hexachlorocyclopentadiene as product from the second effluent;
recovering hydrogen chloride from the second effluent;
introducing at least a portion of the recovered hydrogen chloride into an oxidation zone wherein recovered hydrogen chloride is contacted with oxygen and a molten salt from the hexachlorocyclopentadiene production zone to recover hydrogen chloride by enriching the molten salt in cupric chloride; and
passing molten salt from the oxidation zone to the hexachlorocyclopentadiene production zone.

16. The process of claim 15 wherein the hexachlorocyclopentadiene production zone is operated at a temperature of from about 750° to 1000° F.

17. The process of claim 16 wherein gaseous chlorine is introduced into the hexachlorocyclopentadiene production zone.

18. The process of claim 17 wherein gaseous chlorine is maintained in the hexachlorocyclopentadiene production zone in an amount of from 100 to 500% in excess of stoichiometric requirements for producing hexachlorocyclopentadiene from the chloro substituted cyclopentane exclusive of the chlorine needed for hydrogen removal.

19. The process of claim 18 wherein the effluent withdrawn from the hexachlorocyclopentadiene production zone further contains chlorine, at least a portion of the chlorine present in the effluent being recovered and recycled to the hexachlorocyclopentadiene production zone to maintain the excess of chlorine.

20. The process of claim 19 wherein the hexachlorocyclopentadiene production zone is operated at a temperature of from 800° to 925° F, and a pressure of from 1 to 10 atm. and the oxidation zone is operated at a temperature of from 825° to 900° F and a pressure of from 1 to 10 atm.

21. The process of claim 20 wherein molten salt introduced into the hexachlorocyclopentadiene production zone has a cupric chloride content and is at a temperature which are higher than the cupric chloride content and the temperature of the salt introduced into the oxidation reaction zone and the hexachlorocyclopentadiene production zone is operated at a pressure lower than the pressure of the oxidation zone.

22. The process of claim 21 wherein the molten salt introduced into the hexachlorocyclopentadiene production zone has a cupric chloride content of from about 35 to 50 mole percent.

23. The process of claim 22 wherein a mixed stream of chlorine and hydrogen chloride is recovered from the effluent, a first portion of the mixed stream being introduced into the hexachlorocyclopentadiene production reactor to maintain the excess of chlorine and a second portion being introduced into the oxidation zone to recover net hydrogen chloride generated in the production of hexachlorocyclopentadiene.

24. The process of claim 22 wherein the effluent includes unreacted feed and reaction intermediates convertible to hexachlorocyclopentadiene which are recovered and recycled to the hexachlorocyclopentadiene production reactor.

25. The process of claim 22 wherein excess chlorine is introduced into the initial chlorination reaction and the effluent withdrawn therefrom and introduced into the hexachlorocyclopentadiene production zone includes chlorine.

26. A process for producing hexachlorocyclopentadiene, comprising:

contacting in an initial chlorination zone cyclopentadiene and chlorine to saturate the double bonds and produce a first effluent containing chloro substituted cyclopentane containing at least 4 atoms of chlorine, and hydrogen chloride;

introducing the first effluent into a hexachlorocyclopentadiene production zone wherein the first effluent is contacted with a molten salt mixture of cuprous and cupric chloride, to produce a second effluent containing hexachlorocyclopentadiene, hydrogen chloride and chlorine;

recovering hexachlorocyclopentadiene as product;

recovering chlorine and hydrogen chloride from the second effluent;

passing a portion of the recovered chlorine to the initial chlorination zone to provide at least the chlorine requirements therefor;

passing a further portion of the recovered chlorine to the hexachlorocyclopentadiene production zone to maintain a stoichiometric excess of gaseous chlorine therein;

introducing at least a portion of the recovered hydrogen chloride and fresh feed hydrogen chloride into an oxidation zone wherein fresh feed and recovered hydrogen chloride are contacted with oxygen and molten salt from the hexachlorocyclopentadiene production zone to recover the hydrogen chloride by enriching the cupric chloride content of the molten salt, said fresh feed hydrogen chloride being introduced to provide chlorine requirements for converting cyclopentadiene to hexachlorocyclopentadiene; and passing molten salt from the oxidation zone to the hexachlorocyclopentadiene production zone.

27. The process of claim 26 wherein the hexachlorocyclopentadiene production zone is operated at a temperature of from 750° to 1000° F.

28. The process of claim 27 wherein gaseous chlorine is maintained in the hexachlorocyclopentadiene production zone in an amount of from 100 to 500% in excess of stoichiometric requirements for producing hexachlorocyclopentadiene from the chloro substituted cyclopentane exclusive of the chlorine required for hydrogen atom removal.

29. The process of claim 28 wherein the hexachlorocyclopentadiene production zone is operated at a temperature of from 800° to 925° F, and a pressure of from 1 to 10 atm. and the oxidation zone is operated at a temperature of from 825° to 900° F and a pressure of from 1 to 10 atm.

30. The process of claim 29 wherein molten salt introduced into the hexachlorocyclopentadiene production zone has a cupric chloride content and is at a temperature which is higher than the cupric chloride content and the temperature of the salt introduced into the oxidation reaction zone and the hexachlorocyclopentadiene production zone is operated at a pressure lower than the pressure of the oxidation zone.

31. The process of claim 30 wherein the molten salt introduced into the hexachlorocyclopentadiene production zone has a cupric chloride content of from about 35 to 50 mol percent.

32. The process of claim 31 wherein the effluent includes unreacted feed and reaction intermediates convertible to hexachlorocyclopentadiene which are recovered and recycled to the hexachlorocyclopentadiene production reactor.

33. The process of claim 31 wherein excess chlorine is introduced into the initial chlorination reaction and the effluent withdrawn therefrom and introduced into the hexachlorocyclopentadiene production zone includes chlorine.

* * * * *